US011925496B2

(12) United States Patent
Bolas et al.

(10) Patent No.: US 11,925,496 B2
(45) Date of Patent: Mar. 12, 2024

(54) APPARATUS FOR X-RAY CT SCANNING

(71) Applicant: HALLMARQ VETERINARY IMAGING LTD, Guildford (GB)

(72) Inventors: Nicholas Martin Bolas, Ashford (GB); Eduardo Pallas Lodeiro, Valencia (ES); Laura Moliner Martinez, Castellon (ES); Giedre Podolyak, Guildford (GB); Paul Michael Kurn, Guildford (GB); James Richard Barnett, West Byfleet (GB)

(73) Assignee: HALLMARQ VETERINARY IMAGING LTD, Guildford (GB)

( * ) Notice: Subject to any disclaimer, the term of this patent is extended or adjusted under 35 U.S.C. 154(b) by 416 days.

(21) Appl. No.: 17/296,706

(22) PCT Filed: Nov. 27, 2019

(86) PCT No.: PCT/GB2019/053350
§ 371 (c)(1),
(2) Date: May 25, 2021

(87) PCT Pub. No.: WO2020/109788
PCT Pub. Date: Jun. 4, 2020

(65) Prior Publication Data
US 2022/0022832 A1    Jan. 27, 2022

(30) Foreign Application Priority Data

Nov. 28, 2018  (GB) ...................................... 1819349

(51) Int. Cl.
*A61B 6/03* (2006.01)
*A61B 6/00* (2006.01)
(Continued)

(52) U.S. Cl.
CPC .............. *A61B 6/508* (2013.01); *A61B 6/035* (2013.01); *A61B 6/0407* (2013.01); *A61B 6/107* (2013.01); *A61B 6/4452* (2013.01); *A61B 6/4476* (2013.01)

(58) Field of Classification Search
CPC ........... A61B 6/032; A61B 6/035; A61B 6/04; A61B 6/0407; A61B 6/107; A61B 6/4429; A61B 6/4452; A61B 6/4476; A61B 6/508
See application file for complete search history.

(56) References Cited

U.S. PATENT DOCUMENTS

| 7,224,764 B2 * | 5/2007 | Sukovic ................. A61B 6/032 378/19 |
| 9,986,959 B2 * | 6/2018 | Atzinger .............. F16M 11/105 |

(Continued)

FOREIGN PATENT DOCUMENTS

EP   3 360 484 A1   8/2018

OTHER PUBLICATIONS

International Search Report and Written Opinion of the International Searching Authority dated Feb. 14, 2020.
GB Search Report GB1917282.4, dated Jan. 23, 2020.

*Primary Examiner* — Dani Fox
*Assistant Examiner* — Soorena Kefayati
(74) *Attorney, Agent, or Firm* — Lippes Mathias LLP

(57) ABSTRACT

Apparatus for x-ray CT scanning of an object includes an x-ray generator 1 mounted on a first support 3 on an outer ring 4 and an x-ray detector 2 mounted on a second support 10 on an inner ring 11, and a drive mechanism arranged to rotate the outer and inner rings 4, 11. The outer and inner rings have a first common axis of rotation and the diameter of the outer ring 4 is greater than the diameter of the inner ring 11 The drive mechanism includes a gearing arrangement connecting the outer and inner rings 4,11. The gearing arrangement comprises first and second toothed rotary gears 14,16. The ratio of the number of teeth on the outer and inner rings 4,11 are the same as the ratio of the number of teeth on the first and second rotary gears 14,16 so that the outer and inner rings 4,11 rotate at substantially the same angular speed in the same direction, whereby x-ray radiation emitted by the x-ray generator 1 is directed towards the x-ray detector 2 whilst the first and second supports 3,10, on which the x-ray generator 1 and x-ray detector 2 are respectively mounted, are moving along respective first and second annular concentric paths defined by the outer and inner rings 4,11.

18 Claims, 10 Drawing Sheets

(51) Int. Cl.
 *A61B 6/04* (2006.01)
 *A61B 6/10* (2006.01)

(56) References Cited

U.S. PATENT DOCUMENTS

| | | | |
|---|---|---|---|
| 2009/0185663 A1* | 7/2009 | Gaines, Jr. | A61B 6/0487 |
| | | | 5/601 |
| 2010/0278300 A1* | 11/2010 | Yorkston | A61B 6/032 |
| | | | 378/20 |
| 2011/0228901 A1* | 9/2011 | Yorkston | A61B 6/4441 |
| | | | 378/20 |
| 2013/0039456 A1* | 2/2013 | Seppala | A61B 6/035 |
| | | | 378/4 |
| 2013/0039467 A1* | 2/2013 | Seppala | A61B 6/035 |
| | | | 378/198 |
| 2013/0039479 A1* | 2/2013 | Nyholm | A61B 6/035 |
| | | | 378/196 |
| 2013/0089179 A1* | 4/2013 | Kenny | A61B 6/4208 |
| | | | 378/208 |
| 2015/0313557 A1* | 11/2015 | Mackie | A61B 6/4429 |
| | | | 378/14 |
| 2016/0242719 A1* | 8/2016 | Yorkston | A61B 6/508 |
| 2016/0270747 A1* | 9/2016 | Dirisio | A61B 6/4452 |
| 2016/0361036 A1* | 12/2016 | Ray | A61B 6/032 |
| 2017/0143288 A1* | 5/2017 | Packard | A61B 6/5205 |
| 2018/0028136 A1* | 2/2018 | Manetti | A61B 6/4405 |
| 2018/0055467 A1* | 3/2018 | Cox | A61B 6/4458 |
| 2018/0289348 A1* | 10/2018 | Cox | A61B 6/4078 |

\* cited by examiner

APPARATUS FOR X-RAY CT SCANNING

BACKGROUND OF THE INVENTION

Field of the Invention

The present invention relates to apparatus for x-ray computer tomography (CT) scanning of an object, and in particular for such scanning of a limb of an animal, for example an equine.

Known CT devices for human or animal clinical imaging utilise a single gantry onto which both an x-ray generator and an x-ray detector are mounted. The gantry rotates around the object to be imaged with the x-ray generator facing the detector, such that the x-ray beam emitted by the generator passes through or around the object before reaching the detector. The generator and detector are fixed at approximately the same radial distance from the centre of rotation of the gantry, and they rotate around the centre of rotation at positions diametrically opposite each other.

Such known CT devices in general exist in one of two configurations.

In one configuration, the gantry is "doughnut" shaped, with a central bore large enough to encompass a human patient, or an animal or part of an animal. Such CT devices are in general unsuitable for imaging the limbs of equines or similar large animals, because the animal, or limb of the animal, must be positioned at the centre of the device so that it can be scanned. One possibility is for the animal to be lying down and stationary, which requires the animal to be anaesthetised. In the case of large animals including equines, anaesthesia and the subsequent recovery from anaesthesia carries a significant risk of morbidity or mortality. Alternatively, both limbs must be placed within the device while the animal is standing, or one limb must be placed within the device while the animal stands on the other limbs, both of which create a hazard should the animal fall over or attempt to escape.

In the other common configuration, the gantry is the shape of an inverted "U" with the x-ray generator and detector mounted on opposite arms. Such devices are commonly used for dental imaging of the human head. However they are mechanically unsuitable for scanning animal limbs, because the supporting arms of the CT device collide with the body or limbs of the animal.

Whilst it is possible that a scanning device sufficiently large to accommodate the entire animal could be built, this would be prohibitively expensive.

Description of Related Art

EP3054852A1 discloses an alternative CT scanning device, in which an x-ray generator and an x-ray detector are mounted above a support base and arranged to move in inner and outer annular paths around a limb of an animal standing on the support base. The x-ray generator and x-ray detector are required to be facing each other as they move to enable the required x-ray images of the limb to be captured.

With such an arrangement, two configurations are possible for a human patient or bipedal animal. In the first configuration, both limbs are positioned within the inner ring such that both the x-ray generator and x-ray detector pass around both limbs. In the second configuration, one limb is placed within the inner ring and the other limb is placed just outside the inner ring and between the inner and outer rings. The x-ray generator, following the first annular path, again passes around both limbs. The x-ray detector, following the second and smaller annular path, passes between the limbs. In this configuration the final image is obtained from only the one, centrally located limb. The contralateral limb interrupts the path of the x-ray beam between generator and detector for a small fraction of the full annular path, but any data collected during this period is discarded and the image is reconstructed from data collected over the remaining, slightly less than full 360° rotation.

Imaging a single limb in this way offers practical and cost advantages. Due to the x-ray detector being closer to the limb, the effect of x-ray scatter is reduced and the image is sharper. Also a smaller, and thus less expensive, detector panel can be used, because the cone-shaped beam emanating from the generator expands less over the shorter distance.

For a quadruped animal, such as a horse, a single forelimb or a single hindlimb is imaged in the same way, with the limb to be imaged being placed within the inner ring and the contralateral fore or hind limb being placed between the inner and outer rings. The non-imaged pair of hind or fore limbs are placed outside the outer ring. The x-ray generator, following the first annular path, passes between the fore and hind limbs. The x-ray detector, following the second and smaller annular path, passes between the limb to be imaged and its contralateral partner.

Such an arrangement means that the inner annular path of the x-ray detector and the outer annular path of the x-ray generator cannot be directly connected by a rotating radial element, as it would interfere with the support of the non-imaged leg located between the inner and outer rings.

Providing a means of rotation presents a significant problem, because it is not possible to directly connect the x-ray generator and x-ray detector by any linking rod or arm. Any such link below the level of the generator and detector would at some point have to pass underneath the surface on which the animal stands, making it impossible to support the surface. Any link above the level of the generator and detector would have to pass through one or other limb of the animal.

BRIEF SUMMARY OF THE INVENTION

Accordingly, it is an object of the present invention to provide an improved apparatus for x-ray CT scanning, in which the x-ray generator and detector move as required along the inner and outer annular paths, and also enabling weight-bearing support between the inner and outer rings to be provided.

Accordingly, the present invention consists in apparatus for x-ray CT scanning of an object, the apparatus comprising an x-ray generator mounted on a first support provided on an outer ring and an x-ray detector mounted on a second support provided on an inner ring, and a drive mechanism arranged to rotate the outer and inner rings, wherein the outer and inner rings have a first common axis of rotation and the diameter of the outer ring is greater than the diameter of the inner ring, the first and second supports being positioned diametrically opposite each other with the second support on the far side of the inner ring with respect to the position of the outer ring, wherein the inner surface of the outer ring and the outer surface of the inner ring are formed with teeth, and the drive mechanism includes a gearing arrangement connecting the outer and inner rings, the gearing arrangement comprising first and second toothed rotary gears fixed so as to rotate together about a second common axis of rotation, the first rotary gear having a greater diameter than the second rotary gear, the first rotary gear interengaging with the teeth of the outer ring and the second rotary gear interengaging with the teeth of the inner ring via a third toothed rotary gear or a toothed drive belt, the ratio of the number of teeth on the outer and inner rings being the same as the ratio of the number of teeth on the first and second rotary gears so that the outer and inner rings rotate at substantially the same angular speed in the same direction, whereby x-ray radiation emitted by the x-ray generator is directed towards the x-ray detector whilst the first and second supports, on which the x-ray generator and x-ray detector are respectively mounted, are moving along respective first and second annular concentric paths defined by the outer and inner rings.

The drive mechanism may include a motor arranged to rotate one of the outer ring and the inner ring and thereby to cause rotation of the other one of the outer ring and the inner ring via the gearing arrangement.

Alternatively, the drive may include a motor arranged to rotate a gear of the gearing arrangement and thereby to cause rotation of the outer and inner rings via the gearing arrangement.

The second toothed rotary gear preferably comprises a toothed central hub of the first rotary gear.

In one embodiment, wherein the second rotary gear interengages with the teeth of the inner ring via a toothed drive belt, the toothed drive belt extends around the toothed outer surface of the inner ring and around the toothed central hub. The gearing arrangement may include a tensioner positioned between the outer and inner rings to tension the toothed drive belt.

In another embodiment, wherein the second rotary gear interengages with the teeth of the inner ring via a third toothed rotary gear, the teeth of the third rotary gear interengage with the teeth of the central hub.

The apparatus preferably includes a cable handling mechanism for each of the cables supplying power to the x-ray generator and the x-ray detector. The cable handling mechanism for the cable supplying power to the x-ray generator may comprise a flexible hollow elongate member housing the cable and secured at one end to the support for the x-ray generator so as to move with the support and secured at the other end to a non-moving element of the apparatus, and an annular channel within which the elongate member is constrained and which surrounds the outer ring. The cable handling mechanism for the cable supplying power to the x-ray detector may comprise a flexible hollow elongate member housing the cable and secured at one end to the support for the x-ray detector so as to move with the support and secured at the other end to a non-moving element of the apparatus, and an annular channel within which the elongate member is constrained and which surrounds the inner ring.

The apparatus may include an upper surface supported by side walls and covering the drive mechanism, the upper surface having annular slots formed therein which are coincident with the first and second annular paths, the first and second supports extending upwardly through the respective slots so that the x-ray generator and x-ray detector mounted on the supports are positioned above the upper surface.

The first and second supports may be provided with means for raising and lowering the x-ray generator and x-ray detector mounted on the supports so as to enable objects to be scanned at different heights above floor level.

The apparatus preferably includes control means to enable the drive mechanism to be controlled by an operator. The control means may also be arranged to receive, store and process data from the x-ray detector in such a way as to produce one or more images. Preferably a shield is provided for protecting the operator from X-ray radiation emitted by the x-ray generator.

In one example, wherein the object to be scanned is the limb of an animal, the apparatus may include means for supporting the head of the animal. The control means, the shield and the head supporting means may be provided in a single control station used by the operator.

The provision of the gearing arrangement which is fixed relative to the rotation of the outer ring means that adequate supports can be provided between the inner and outer rings beneath the upper surface, so as to support the weight of a large animal such as a horse standing on the upper surface.

Additionally, in known configurations of the CT apparatus, the entire CT device is most often large in size and heavy in weight, and is installed in a fixed location in a dedicated scanning room.

In contrast, the apparatus according to the present invention can be made portable and able to be moved conveniently. Situations in which this may be of benefit include moving the apparatus to the side of an examination room when not in use, lifting the apparatus to rest against the wall of the examination room when not in use, and installing the apparatus in a suitable vehicle for use at multiple locations.

Accordingly, in one configuration, the device may be fitted with wheels underneath the enclosure. In another configuration, the supports for the x-ray generator and x-ray detector may be detachable from the remaining apparatus and the electrical connections for power and signals may use connectors, such that the x-ray generator and x-ray detector may be detached and the apparatus stored so as to lean against a wall or some other place.

BRIEF DESCRIPTION OF THE DRAWINGS

The invention will now be described by way of example with reference to the accompanying drawings, in which.

DETAILED DESCRIPTION OF THE INVENTION

Figure 1:
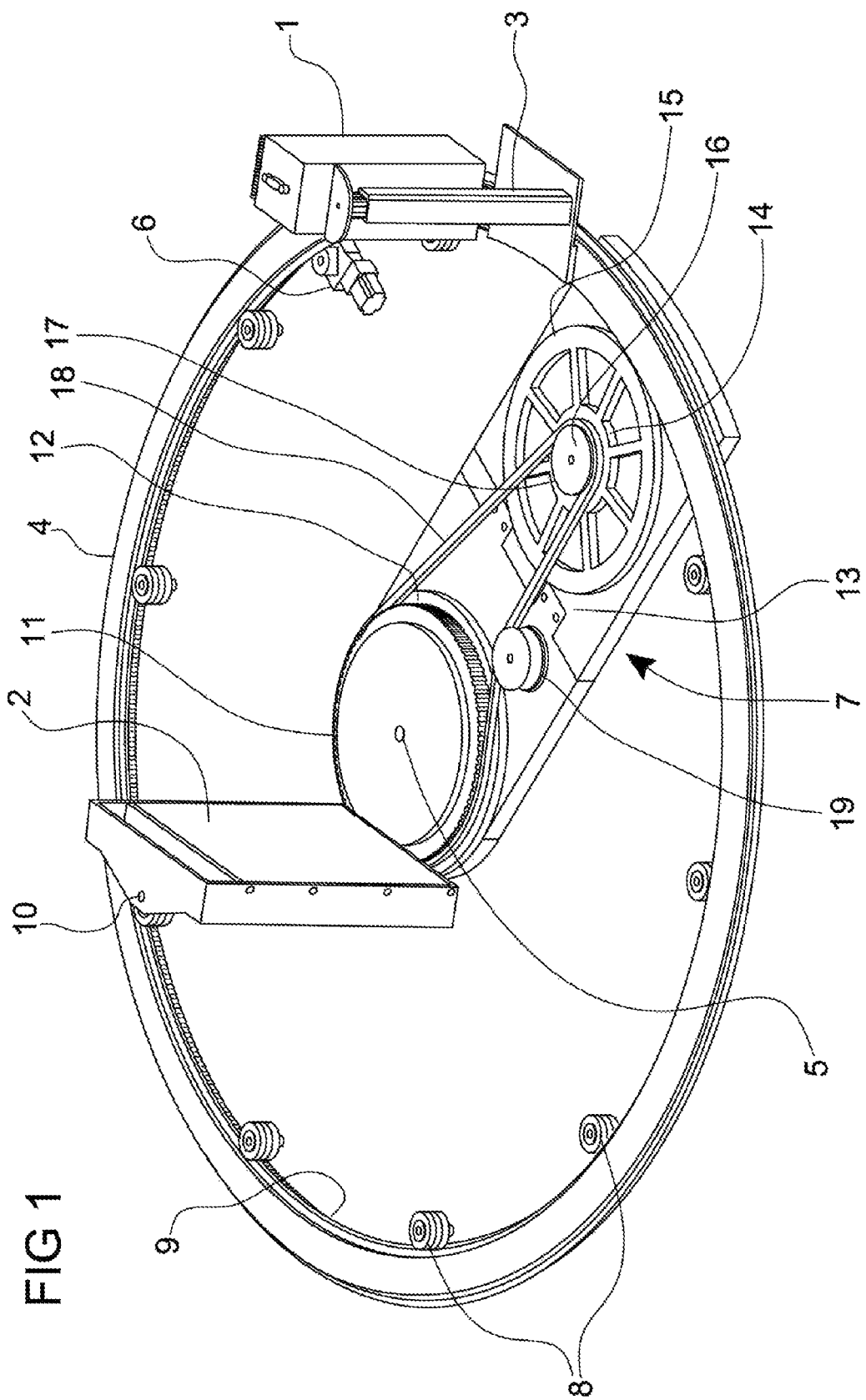
FIG. 1 shows a schematic view of one embodiment of the apparatus including an x-ray generator and x-ray detector and a drive mechanism according to the present invention.

Referring to the drawings, there is shown an apparatus for x-ray CT scanning of an object, such as a limb of an animal. The apparatus comprises an x-ray generator 1 and an x-ray detector 2 positioned facing the x-ray generator so that x-ray radiation emitted by the generator is directed towards the detector. The x-ray generator 1 is mounted on a support 3 which is fixed to an outer ring 4. The outer ring 4 is driven to rotate about a centre of rotation 5 by a motor 6 of a drive mechanism 7, and the outer ring 4 is supported by a plurality of roller bearings 8 engaging at spaced intervals with inner surface 9 of the outer ring 4. The x-ray detector 2 is mounted on a support 10 fixed to an inner ring 11 which is also driven by the drive mechanism 7 to rotate about the centre of rotation 5. The rotatable outer and inner rings 4, 11 therefore define respective concentric outer and inner annular paths along which the supports 3, 10 and the x-ray generator 1 and detector 2 mounted on the supports are constrained to move, the outer ring (and path) having a larger diameter than the inner ring (and path).

The supports 3, 10 are positioned diametrically opposite each other on the respective rings 4, 11, with the support 10 positioned on the far side of the inner ring 11 relative to the position of the support 3 on the outer ring 4.

The drive mechanism 7 is arranged to rotate the outer and inner rings 4, 11 at substantially the same angular speed in the same rotational direction, so that the x-ray generator 1 and x-ray detector 2 remain facing each other whilst moving along their respective annular paths.

The inner surface 9 of the outer ring 4 and outer surface 12 of the inner ring 11 are each formed with teeth, the toothed inner surface 9 engaging with the motor 6 to rotate the outer ring 4. The drive mechanism 7 includes a gearing arrangement 13 for causing the inner ring 11 to rotate at the same angular speed and in the same direction as the outer ring 4. The gearing arrangement 13 includes a toothed rotary gear 14 mounted for rotation between the outer and inner rings 4, 11, with toothed outer surface 15 of the gear 14 positioned to engage with the toothed inner surface 9 of the outer ring 4. The gear 14 has a central hub 16 with a toothed outer surface 17. The drive mechanism 7 also includes a toothed belt drive 18 which engages around the toothed outer surface 17 of the central hub 16 of the gear 14 and around the toothed outer surface 12 of the inner ring 11. A tensioner 19 is also provided in engagement with the belt drive 18.

With this arrangement, the motor 6 drives the outer ring 4 to cause it to rotate, which in turn rotates the gear 14 and central hub 16, which thus rotates the inner ring 11 via the belt drive 18. In this manner, with appropriate sizing of the rings and gear, the outer and inner rings can be made to rotate at the same angular speed in the same direction.

In order that the inner and outer toothed rings 4,11 rotate at substantially the same rate the ratio between the number of teeth on the outer ring 4 to the number of teeth on the inner ring 11 must be the same as the ratio between the number of teeth on the toothed rotary gear 14 and its toothed central hub 16.

Examples of combinations of gears are in the table below, the numbers referring to the number of teeth on each gear:

|  | Example 1 | Example 2 | Example 3 | Example 4 |
|---|---|---|---|---|
| Outer ring 4 | 113 | 226 | 288 | 288 |
| Inner ring 11 | 113 | 113 | 144 | 96 |
| Rotary gear 14 | 80 | 80 | 80 | 90 |
| Central hub gear 16 | 80 | 40 | 40 | 30 |

In example 1, the number of teeth on the outer ring 4 is a prime number, so the number of teeth on the inner ring must be the same or a multiple, and it cannot be less. In this example, the number of teeth on both rings 4,11 is the same, and therefore the size of gear tooth on the inner ring will be smaller than on the outer ring 4. Available gear tooth sizes will determine the diameters of the rings. The rotary gear 14 and central hub 16 maintain the 1:1 ratio of tooth count, and will also need to have matching gear tooth sizes.

In example 2, the inner ring 11 remains as in example 1, and the outer ring 4 has a simple multiple (×2) number of teeth. The rotary gear 14 and central hub 16 match the 2:1 ratio.

In examples 3 and 4, the outer and inner rings 4, 11 have a non-prime number of teeth, so a wider range of ratios is possible, with the ratios in these examples being 2:1 and 3:1.

Figure 2:
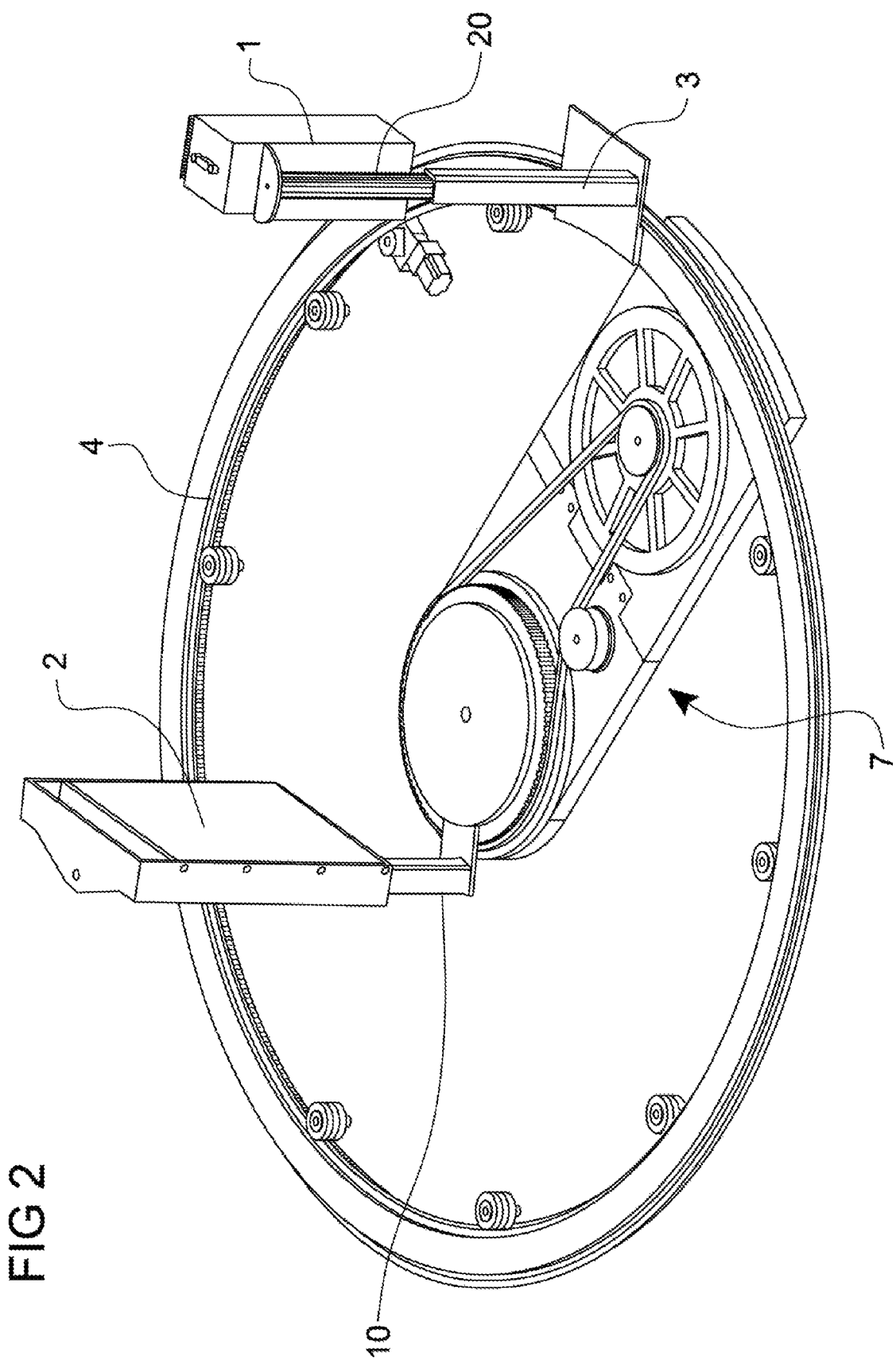
FIG. 2 shows a view of the embodiment with the x-ray generator and x-ray detector in a raised position.

As shown in FIG. 2, the supports 3, 10 are provided with height adjusters 20, which are preferably telescopic, to enable the x-ray generator 1 and x-ray detector 2 to be raised and lowered relative to the floor on which the apparatus is placed. This enables any part of the animal limb from floor level upward to be scanned until such point as the detector or generator interferes with another part of the body of the animal.

Figure 3:
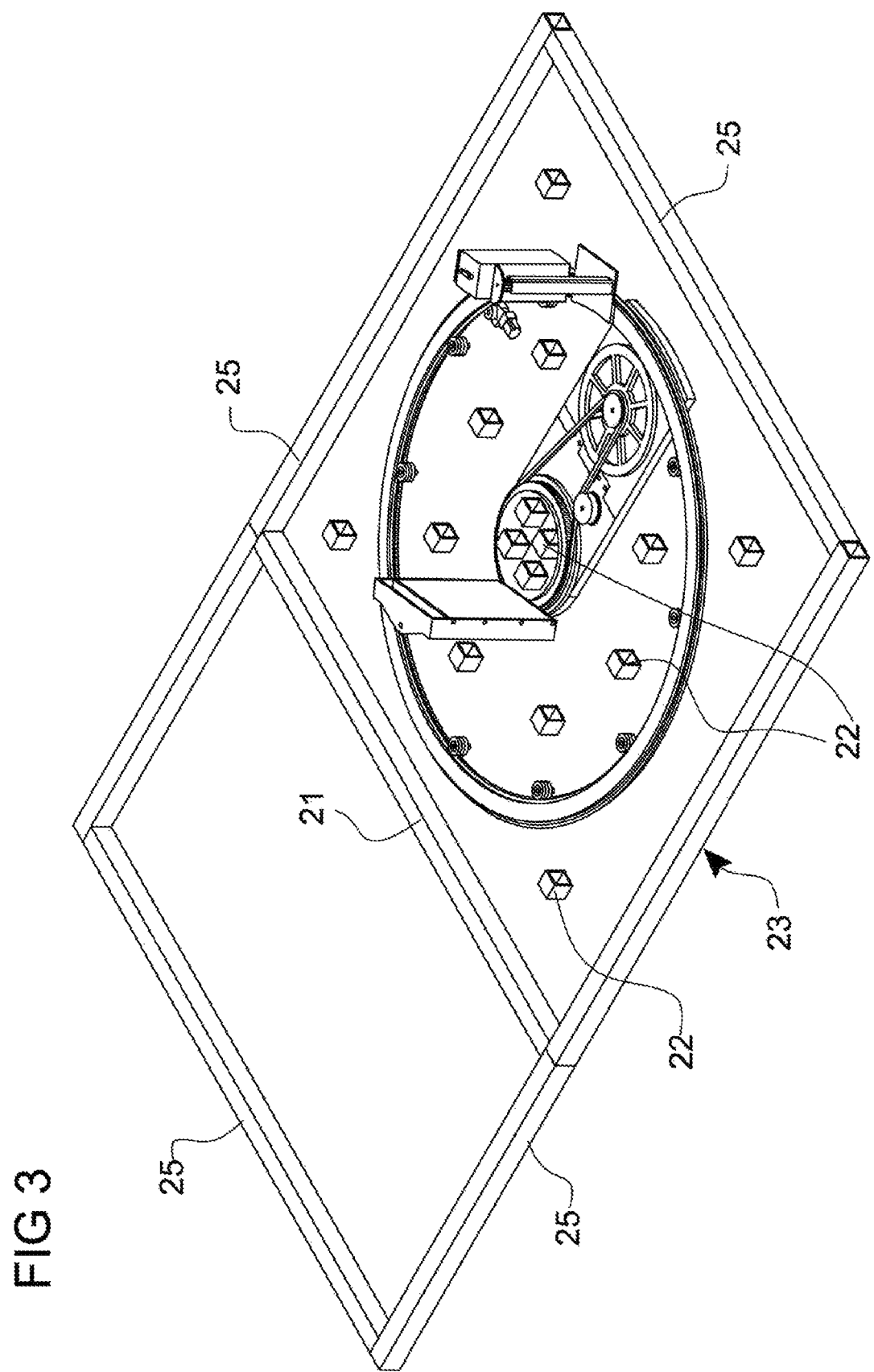
FIG. 3 shows a view of the apparatus accommodated within a shallow enclosure.
Figure 4:
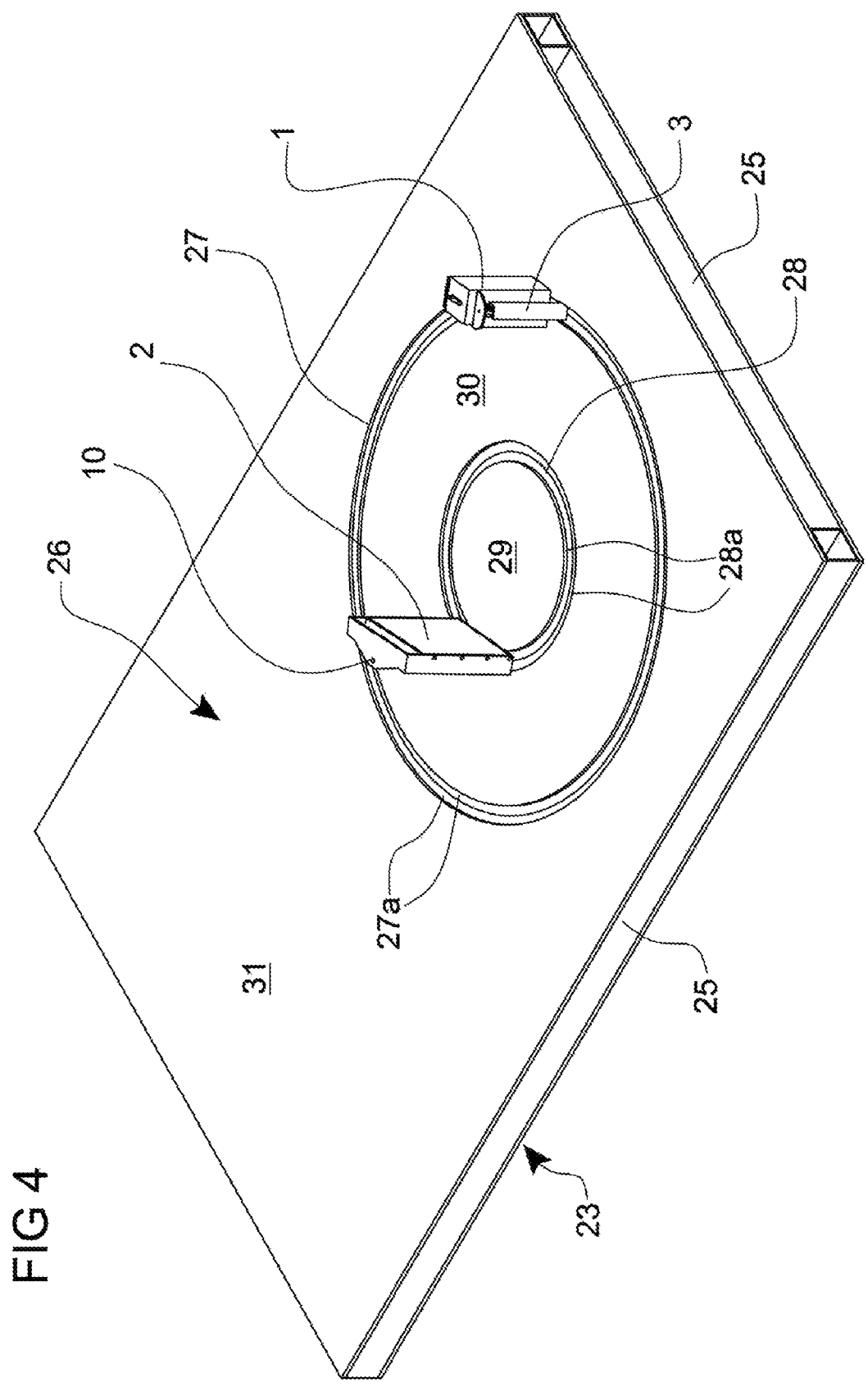
FIG. 4 shows a view of the enclosure covered by an upper surface.

FIG. 3 shows a rectangular enclosure or box 23 having a base 24 and side walls 25, which can accommodate the apparatus shown in FIGS. 1 and 2. The enclosure 23 includes a transverse support 21 extending across the width of the enclosure and a plurality of block supports 22 at spaced intervals surrounding and within the inner and outer rings. The supports 21 and 22 provide support for an upper surface 26, as shown in FIG. 4, which is sufficiently secure for a large animal, particularly a horse, to stand on above the areas within the inner and outer rings. The provision of these supports is possible due to the gearing arrangement being in a fixed position relative to the rotation of the outer ring. If, instead of the gearing arrangement, an interconnection between the inner and outer rings was provided which rotates with the outer ring, it would not be possible to have any supports 22 within the area between the inner and outer rings.

FIG. 4 shows the enclosure 23 with the upper surface 26 supported by the side walls 25 and supports 21, 22 and covering the drive mechanism and rings. The upper surface 26 is formed with two annular slots 27, 28, which are coincident respectively with the outer ring 4 and inner ring 11, to enable the supports 3, 10 to extend upwardly through the slots and the x-ray generator 1 and x-ray detector 2 mounted on the supports to move above the upper surface 26. The upper surface 26 therefore comprises a central disc portion 29 surrounded by the inner annular slot 28, an annular portion 30 surrounding the inner annular slot 28 and being surrounded by the outer annular slot 27, and an outer portion 31 surrounding the outer annular slot 27. Thus, the upper surface 26 forms a platform on which an animal or other object to be scanned can stand.

Brushes 27*a* are attached to the two edges of the outer annular slot 27 to help prevent dirt and solid materials falling through the slot and interfering with the moving ring 4. Support 3 attached to the x-ray generator 1 extends upward between the brushes 27*a* pushing the brush hairs aside as it moves around the annular slot 27 and allowing the brush hairs to return into the slot 27 once it has passed. Similarly brushes 28*a* are attached to the two edges of the inner annular slot 28 to help prevent dirt and solid materials falling through the slot and interfering with the moving inner ring 11. Support 10 attached to the x-ray detector 2 extends upward between the brushes 28*a* pushing the brush hairs away as it moves around the annular slot 28 and allowing the brush hairs to return into the slot 28 once it has passed.

Supporting components, such as a middle wall 32 (shown in FIG. 3), are included within the enclosure 23, so that the upper surface 26 is secure and sufficient to support the weight of a large animal, whilst still allowing a full 360° free movement of the x-ray generator 1, the x-ray detector 2, and their respective supports 3, 10 through the slots 27, 28. Space within the enclosure 23 not occupied by moving parts of the apparatus or support components may be used to contain free cable released from, or required by, the moving parts of the apparatus as they rotate.

Figure 5:
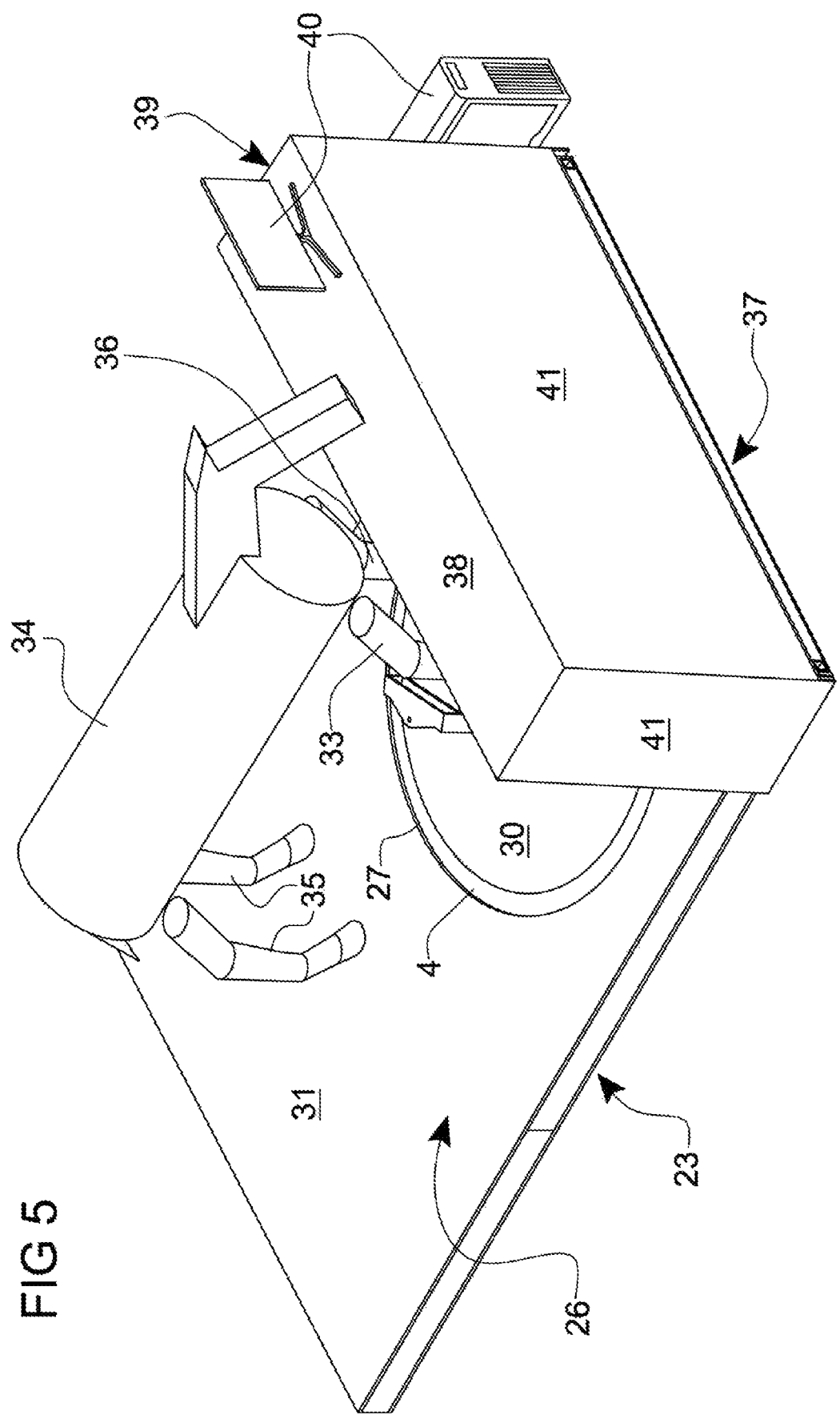
FIG. 5 shows a view of the apparatus in use.

FIG. 5 shows the apparatus in use for CT scanning of the right fore leg 33 of an equine 34. The animal is made to stand on the upper surface 26 with its hind legs 35 positioned on the outer part 31 of the upper surface 26, its right fore leg 33 to be scanned positioned on the central disc portion 29 and its left fore leg 36 positioned on the annular portion 30. During rotation of the outer and inner rings 4, 11 by the drive mechanism 7, the x-ray generator 1 is constrained to move around both fore legs 33, 36 and between the fore legs 33, 36 and hind legs 35, and the x-ray detector 2 is constrained to move around only the right fore leg 33 to be scanned and between the right and left fore legs. The x-ray generator 1 and x-ray detector 2 can be moved through any angle up to 360° or more, whilst moving at substantially the same angular speed in the same direction and facing each other.

The enclosure 23 is sufficiently large and robust that the animal can stand above the apparatus, with the limb to be scanned placed approximately at the centre of rotation 5. The upper surface 26 is of low height such that the animal can readily step onto it and the risk of injury if it were to step off is small. The base 24 rests on the ground or floor where the apparatus is installed. The side walls 25 connect the base 24 to the upper surface 26 and provide protection to the interior apparatus. In the preferred configuration, the height of the enclosure 23 is approximately 10-20 cm, and the side walls 25 are vertical or sloped in order to provide a convenient and safe step up for the equine or other animal.

Figure 6:
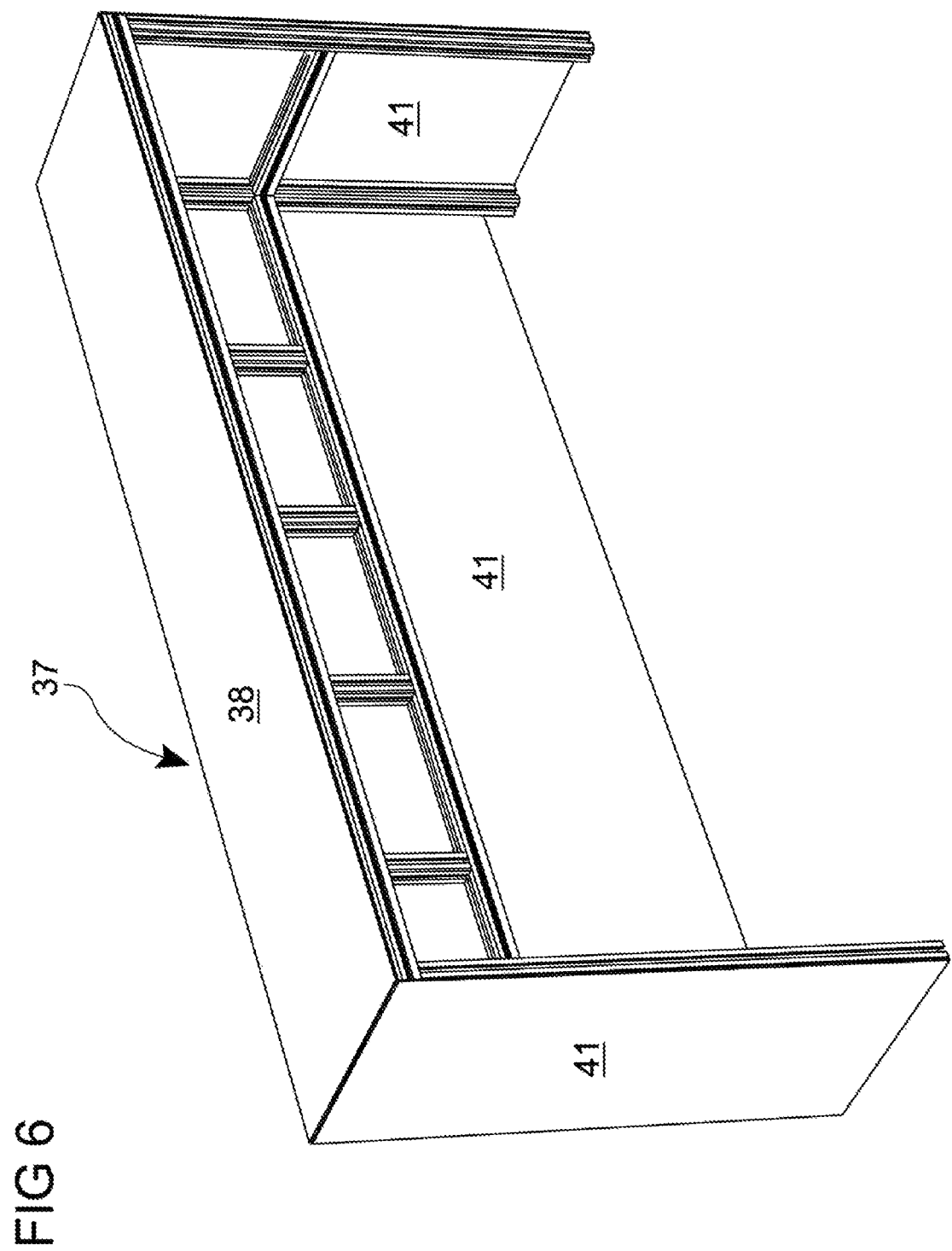
FIG. 6 shows another view of part of the apparatus shown in FIG. 5.

A screen 37, shown in FIGS. 5 and 6, is positioned around one end of the enclosure 23 conveniently adjacent the head end of the animal, with an operator (not shown) positioned at an outer side of the screen 37 to provide protection of the operator from x-ray radiation emitted by the x-ray generator. Upper surface 38 of the screen 37 can be used as a headrest for the animal if the animal has been sedated, and the upper surface 38 can also include a control station 39 used by the operator. The control station 39 may comprise one or more computers 40, to which the x-ray generator 1, x-ray detector 2 and the motor 6 are connected. The screen 37 is provided with three side walls 41 dimensioned to fit around the end of the enclosure 23, as shown in FIG. 6.

One function of the computer(s) is to control movement of the x-ray generator and detector. Another function of the computer(s) is to receive, store and process data from the x-ray detector in such a way as to produce one or more images.

A single operator can position and hold the animal, and control the apparatus by means of the control station 39. The control includes features to start and stop scanning, and to locate the x-ray generator and detector to a convenient starting position. The control includes a means to determine the location of the x-ray generator and detector, and to cause them to move rapidly to the sides of the animal if necessary, so that the animal can escape with minimum risk of damage.

The remote control station 39 thus allows the operator both to hold the head of the animal and to control the scanning apparatus while remaining screened from x-ray radiation.

Figure 7:
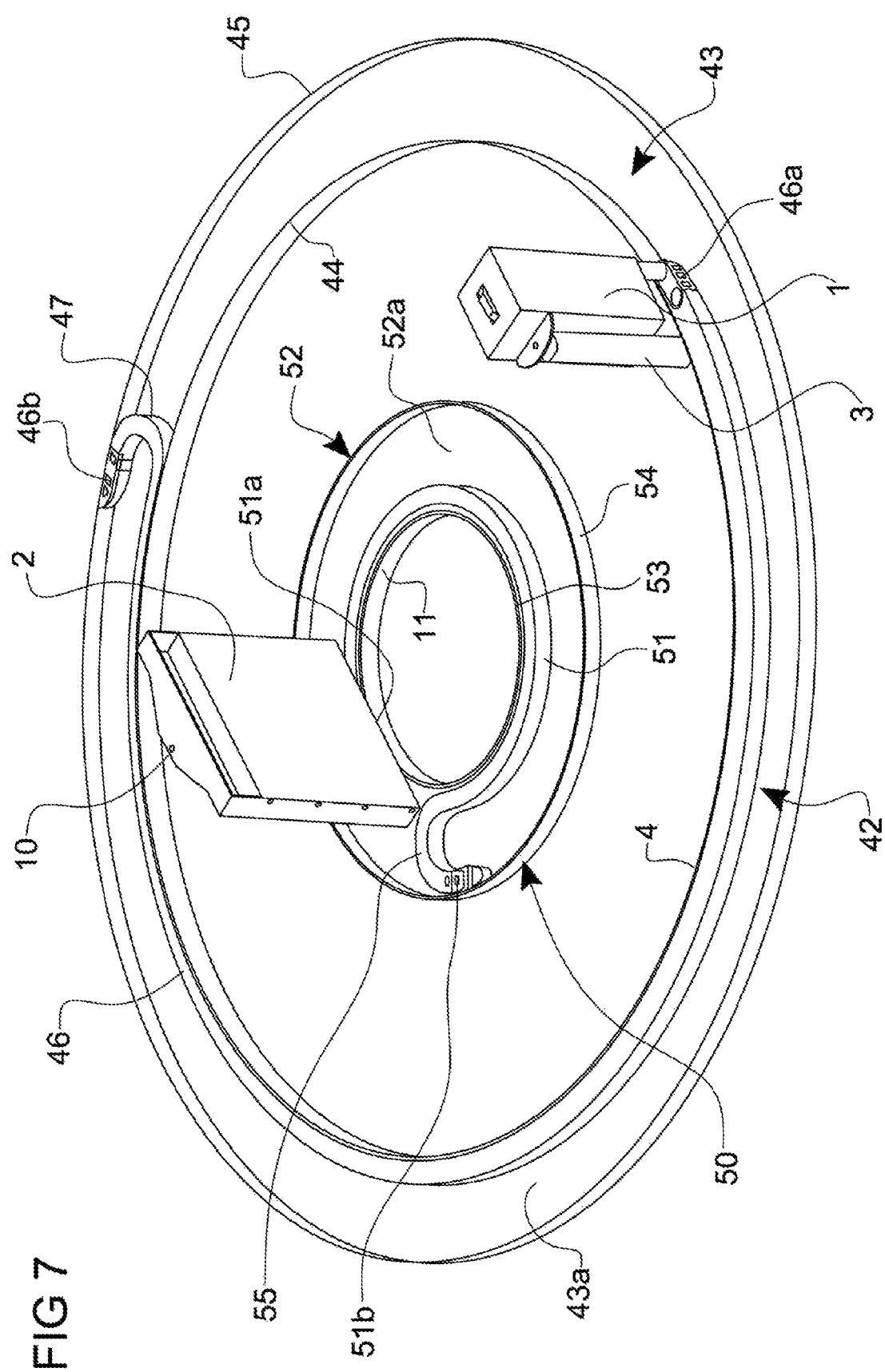
FIGS. 7 and 8 show an embodiment of the apparatus including mechanisms for handling the cables for supplying power to the x-ray generator and x-ray detector.
Figure 8:
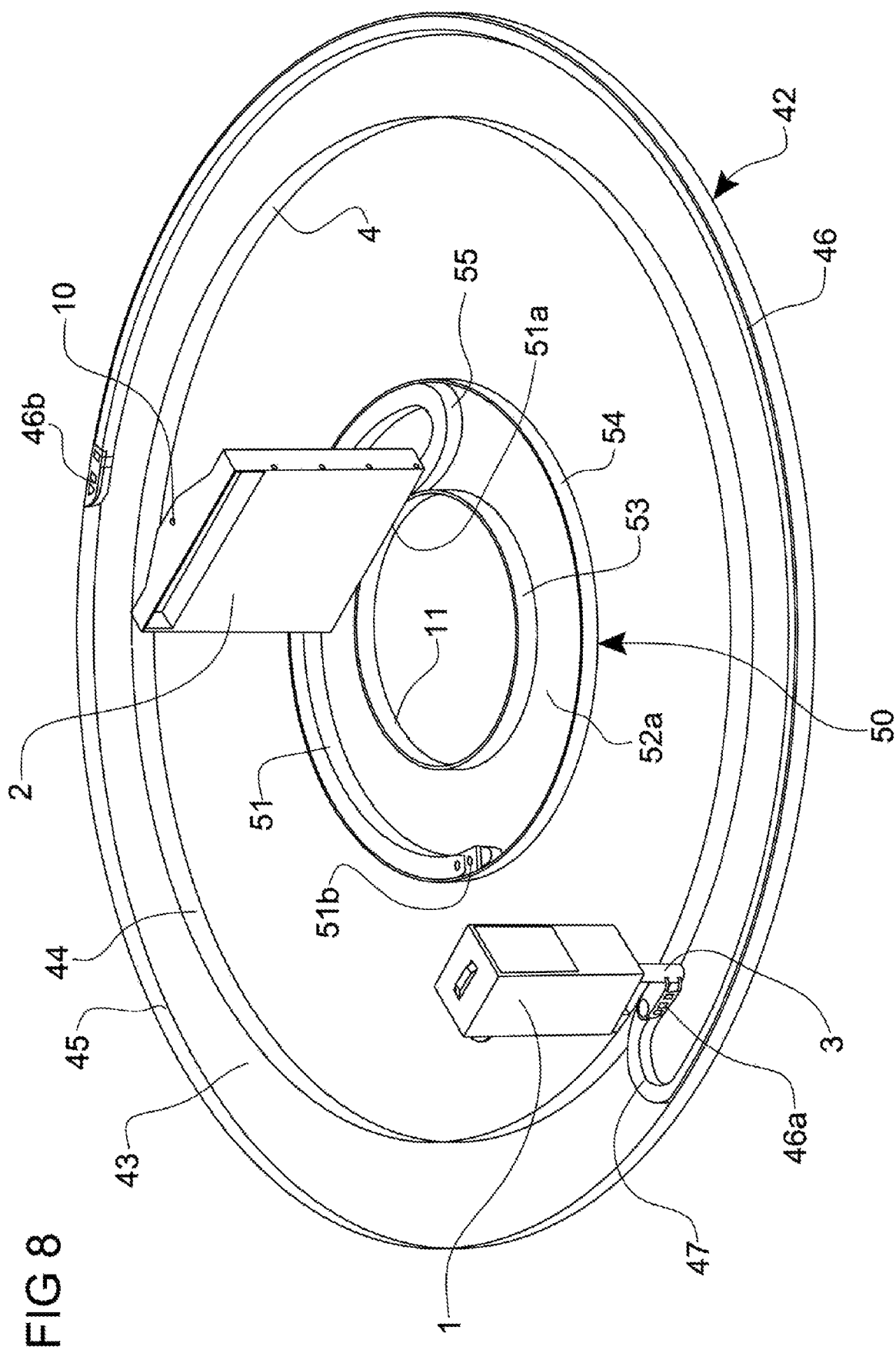

FIGS. 7 and 8 show an embodiment of the apparatus including two cable handling mechanisms 42, 50 to handle the cables supplying power to the x-ray generator 1 and x-ray detector 2 respectively during their movement along their respective annular paths. Both of the cable handling mechanisms are accommodated within the enclosure 23 below the upper surface (not shown). The cable handling mechanism 42 for the x-ray generator 1 is positioned outside the outer ring 4, and the cable handling mechanism 50 for the x-ray detector 2 is positioned outside the inner ring 11 and inside the outer ring 4.

The cable handling mechanism 42 for the x-ray generator 1 may comprise a flexible, hollow chain 46 attached at one end 46a to the support 3 fixed to the x-ray generator 1 so as to move with the support 3. One or more flexible electrical cables [not shown] are passed through the chain 46. The chain 46 is constrained within an annular channel 43 comprising a fixed flat ring 43a and inner and outer side walls 44,45. The other end 46b of the chain 46 is secured to a non-moving element associated with the side walls and upper surface of the whole apparatus, such as the outer side wall 45. The inner diameter of the channel 43 is slightly larger than the diameter of the outer rotating ring 4, such that it does not obstruct the rotation. The outer diameter of the channel 43 provides sufficient space between the inner and outer side walls 44,45 for the chain 46 to fold into a U-shaped loop. The side walls 44,45 are of sufficient height to constrain the chain 46 between the inner and outer side walls. The chain 46 is of sufficient length that it is fully extended at each extreme end of the movement of the x-ray generator 1 around the outer ring 4. As the x-ray generator 1 moves along its annular path from one extreme to the other, the chain 46 first folds into a U-shape loop, and then extends in the opposite direction to reach full extension at the opposite extreme end of the range of movement.

The cable chain 46 is composed of hollow cuboid sections with hinged links each one such that the chain can bend on a smaller radius in one direction than in the opposite direction. In FIG. 7 the mechanism is shown in a fully anti-clockwise position. Further movement in an anti-clockwise direction would reach beyond the length of the chain 46 and is prevented by limit switches (not shown) and the motor controller. Movement in a clockwise direction first pushes the chain 46 against the outer wall 45, and then pushes the tight bend 47 around the channel 43 constrained between the walls 44 and 45. Rotation can continue in a clockwise direction until the attachment 46a of the chain 46 to the x-ray generator 1 reaches the tight bend, at which point further motion is again prevented by limit switches (not shown) and the motor controller. The full length of the cable chain 46 extends at least 270° around the channel 43, and is thus sufficient for the x-ray generator 1 to rotate around the central axis of the mechanism by at least 540°.

The cable handling mechanism 50 for the x-ray detector 2 may comprise a flexible, hollow chain 51 attached at one end 51a to the support 10 fixed to the x-ray detector 2, and at the other end 51b to a non-moving element associated with the side walls and upper surface of the whole apparatus, such as outer wall 54. One or more flexible electrical cables (not shown) are passed through the chain 51. The chain 51 is constrained by an annular channel 52 comprising a fixed flat ring 52a and inner and outer side walls 53,54. The inner diameter of the channel 52 is slightly larger than the diameter of the inner rotating ring 11, such that it does not obstruct the rotation. The outer diameter of the channel 52a provides sufficient space between the inner and outer side walls 53,54 for the chain 51 to fold into a U-shaped loop. The side walls 53,54 are of sufficient height to constrain the chain 51 between the inner and outer side walls. The chain 51 is of sufficient length that it is fully extended at each extreme end of the movement of the x-ray detector 2 along its annular path around the inner ring. As the x-ray detector 2 moves around its path from one extreme to the other, the chain 51 first folds into a U-shape loop, and then extends in the opposite direction to reach full extension at the opposite extreme end of the range of movement.

The cable chain 51 is composed of hollow cuboid sections with hinged links each one such that the chain 51 can bend on a smaller radius in one direction than in the opposite direction. In FIG. 7 the mechanism is shown in a fully anti-clockwise position. Further movement in an anti-clockwise direction would reach beyond the length of the chain 51 and is prevented by limit switches (not shown) and the motor controller. Movement in a clockwise direction first pushes the chain 51 against the outer wall 54, and then pushes the tight bend 55 around the channel 52 constrained between the walls 53 and 54. Rotation can continue in a clockwise direction until the attachment 51a of the chain 51 to the x ray detector 2 reaches the tight bend, at which point further motion is again prevented by limit switches (not shown) and the motor controller. The full length of the cable chain 51 extends at least 270° around the channel 52, and is thus sufficient for the x-ray detector 2 to rotate around the central axis of the mechanism by at least 540°.

In FIG. 8, the cable handling mechanisms 42,50 are shown in the other extreme positions of the x-ray generator 1 and x-ray detector 2, as compared to their positions shown in FIG. 7. The cable handling mechanisms allow the outer and inner rings to rotate through at least 360° and up to about 540°. Thus, a full 360° rotation from each of the two starting positions can be obtained, one for the left limb and one for the right limb, each 180° apart such that the x-ray detector can always start its rotation outside the limb to be examined.

The cables of the x-ray generator 1 and x-ray detector 2 are preferably connected to the control computer 40 as well as the power supply, for transmission of control and data signals as well as power. The cables may be single multi-core, or a group of cable collected together in a flexible trunking (not shown)

Figure 9:
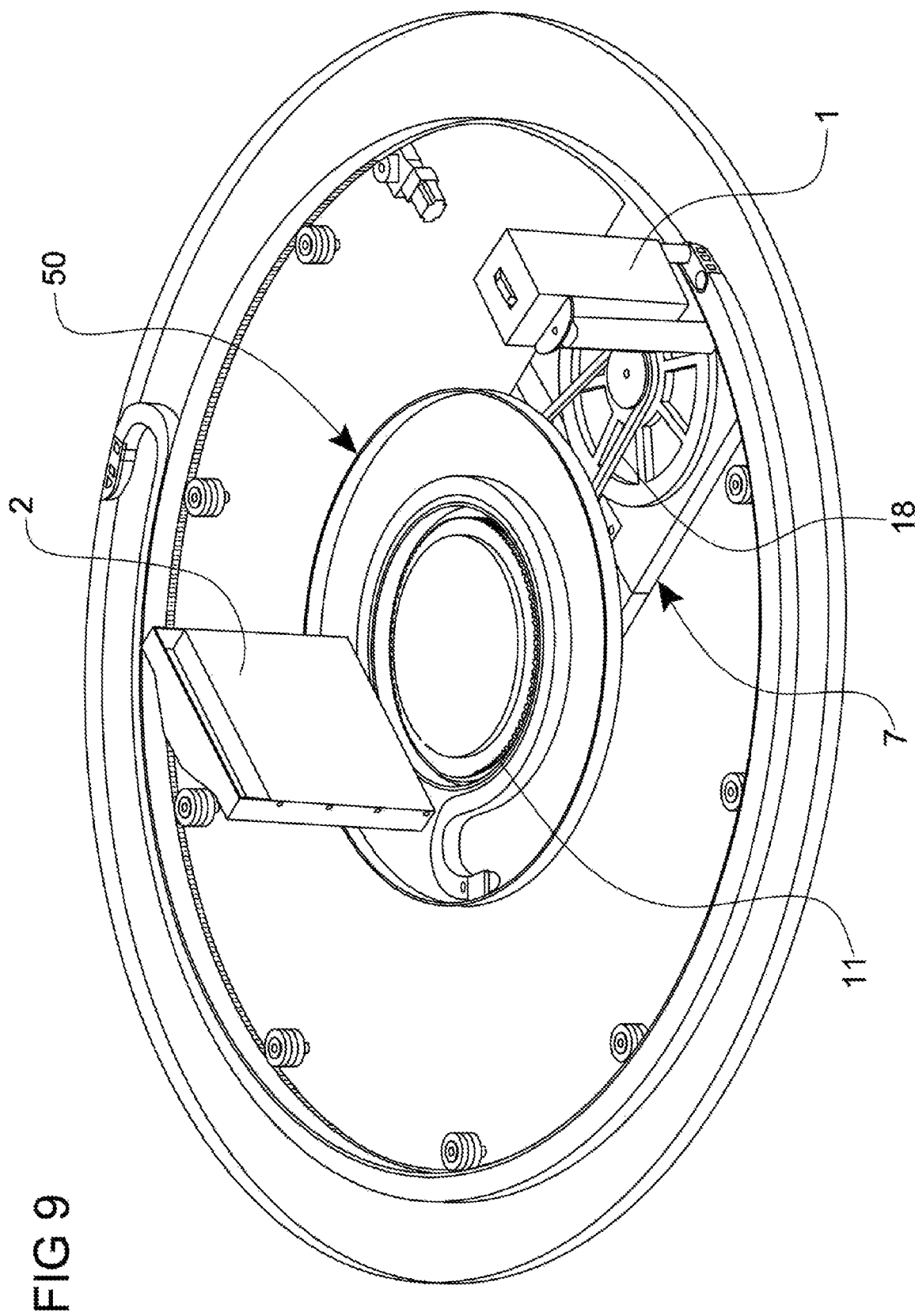
FIG. 9 shows a view of the embodiment with both the drive mechanism and cable handling mechanisms together.

FIG. 9 shows both the drive mechanism and cable handling mechanisms together in the same apparatus. It can be seen from this Figure that the cable handling mechanism 50 is in a fixed position over the drive mechanism 7, whilst the toothed belt drive 18 is free to move beneath it, thereby rotating the inner ring 11.

Figure 10:
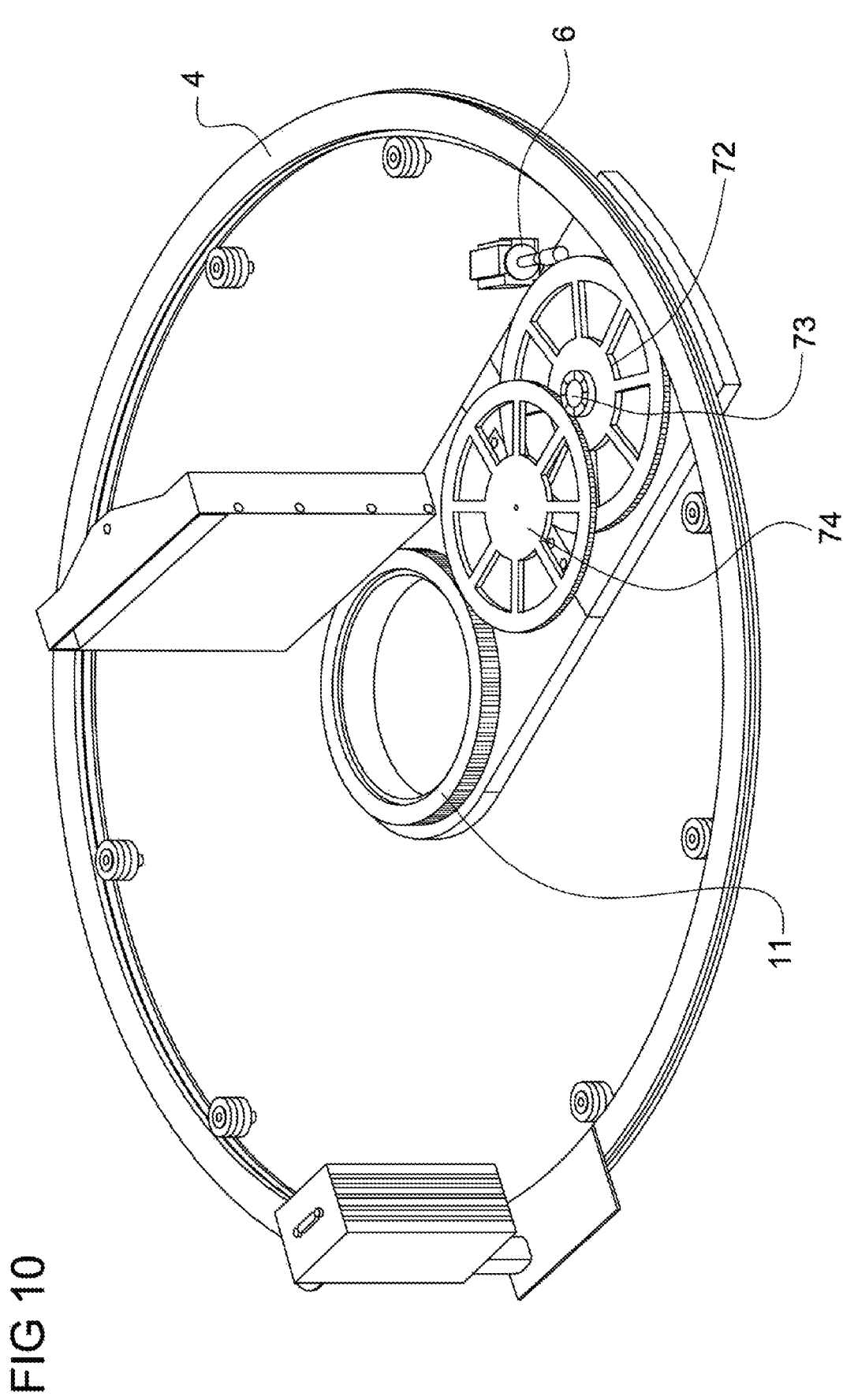
FIG. 10 shows an alternative embodiment of a drive mechanism for the apparatus.

FIG. 10 shows an alternative embodiment of the gearing arrangement comprising three toothed rotary gears 72, 73, 74. The outer toothed surface of the first gear 72 engages with the inner toothed surface of the outer ring 4. This gear 72 is fixed rigidly to the second toothed gear 73 of smaller diameter rotating around the same axis as the first gear 72. The outer toothed surface of the second gear 73 engages with the outer toothed surface of the third gear 74. The outer toothed surface of the third gear 74 engages with the outer toothed surface of the inner ring 11. The diameters and the number of teeth of the first, second and third rotary gears are chosen such that the inner and outer rings rotate at substantially the same angular speed and in the same direction. To achieve this, the ratio of numbers of teeth on the inner and outer rings and on the first and second rotary gears are the same as in the embodiment of FIGS. 1 to 3. In this embodiment, the motor 6 engages with the first gear 72 to drive the gearing arrangement and thereby rotate the rings.

The motor 6 may be provided with a worm gear to engage with the outer toothed surface of the first gear 72, so that the drive comes from the centre of the motor rather than the top of the motor. This enables the motor to fit more easily into the shallow space within the enclosure.

Robust covers (not shown) made of a material with a low absorption of x-rays can be provided to protect the x-ray generator and source, and the respective supports. Such covers preferably extend over only a short distance, such that the animal always has freedom to escape. In particular they do not cover the full 360° rotation.

The x-ray detector 2 is preferably close to the limb to be secured, with the x-ray generator 1 creating a beam of a relatively narrow angle from further away.

The x-ray generator 1 and detector 2 are preferably standard supplier items made for CT applications. Specifically, they are designed to run for a period of time (a CT scan generally takes 1 to 2 minutes) and the detector is designed to output a series of frames in quick succession.

The present invention therefore provides apparatus for x-ray CT scanning which is particularly suitable for scanning a limb of a large animal such as an equine. The apparatus is capable of scanning a single limb whilst the animal is in its usual standing posture, thus minimising any discomfort to the animal. X-ray radiation emitted by the x-ray generator 1 passes through the limb being scanned and is detected by the plate of the x-ray detector 2, as the x-ray generator and detector are both moved around the limb. The images produced by the scan can be reconstructed, without the relatively small section of the annular path where imaging of the limb to be scanned is obscured by the contralateral limb, so that imaging can be achieved from slightly less than a full 360° view.

If the x-ray generator and detector both surrounded both fore limbs, then both limbs would be imaged together. Otherwise, at the points where the generator and detector are in alignment with the two limbs, one limb would obstruct the x-ray beam and prevent the detector from collecting sufficient data. Also, imaging both limbs together would require a larger detector panel and a higher power x-ray generator, thereby increasing cost. The size of the detector panel would also have to be large enough to capture the entire enlarged projection of the limb as the cone of x-rays from the generator expands with distance, first reaching the limb and then the detector.

On the other hand, a complete scanning apparatus small enough to surround only one limb is also not feasible. This is because an equine or other animal is only able to stand still for a reasonable period of time if it is standing on all four limbs, and the distance between one limb and its contralateral limb cannot be extended much beyond the normal stance of the animal. Additionally, currently available x-ray generators are too large to fit between the contralateral limbs at the distance required between the generator and limb to be scanned to obtain the correct imaging. The cone of x-rays produced by the x-ray generator would have to be very wide in order to encompass the entire width of the limb from a close distance. The enlargement effect of such a wide cone would increase the size of the detector required, to the point where it may also not fit between the limbs and would increase cost.

Although one embodiment of the invention has been described, modifications may be made without departing from the scope of the appended claims. In an alternative embodiment, the enclosure may not be included so that the animal stands with its limb to be scanned within the inner ring and its contralateral limb positioned between the outer and inner rings. Other alternative gearing arrangements can be used, as long as the outer and inner rings are caused to rotate in the same direction at substantially the same angular speed. In at least one position in the gearing arrangement, there needs to be two gears of different sizes rigidly fixed together on the same rotational axis, so as to provide the gearing ratio necessary for the outer and inner rings to rotate at the same angular speed. The apparatus may also be used for scanning other objects apart from the limbs of an animal.

The invention claimed is:

1. An apparatus for x-ray CT scanning of an associated object, the apparatus comprising:
   an x-ray generator mounted on a first support provided on an outer ring, an x-ray detector mounted on a second support provided on an inner ring, and a drive mechanism arranged to rotate the outer and inner rings, wherein:
   the outer and inner rings have a first common axis of rotation and a diameter of the outer ring is greater than a diameter of the inner ring,
   the first and second supports being positioned diametrically opposite each other with the second support on a far side of the inner ring with respect to a position of the outer ring,
   an inner surface of the outer ring and an outer surface of the inner ring are formed with teeth,
   the drive mechanism includes a gearing arrangement connecting the outer and inner rings,
   the gearing arrangement comprises toothed, first and second rotary gears fixed so as to rotate together about a second common axis of rotation,
   the first rotary gear having a greater diameter than the second rotary gear,
   the first rotary gear interengaging with the teeth of the outer ring and the second rotary gear interengaging with the teeth of the inner ring via a toothed, third rotary gear or a toothed drive belt,
   a ratio of a number of teeth on the outer and inner rings being the same as a ratio of a number of teeth on the first and second rotary gears so that the outer and inner rings rotate at substantially a same angular speed in a same direction, and
   wherein x-ray radiation emitted by the x-ray generator is directed towards the x-ray detector while the first and second supports, on which the x-ray generator and x-ray detector are respectively mounted, are moving along respective first and second annular concentric paths defined by the outer and inner rings.

2. The apparatus as claimed in claim 1, wherein the drive mechanism includes a motor arranged to rotate one of the outer ring and the inner ring and which causes rotation of an other one of the outer ring and the inner ring via the gearing arrangement.

3. The apparatus as claimed in claim 1, wherein the drive mechanism includes a motor arranged to rotate a gear of the gearing arrangement and which causes rotation of the outer and inner rings via the gearing arrangement.

4. The apparatus as claimed in claim 1, wherein the second rotary gear comprises a toothed central hub of the first rotary gear.

5. The apparatus as claimed in claim 1, including a cable handling mechanism including flexible, hollow sections for cable supplying power to the x-ray generator and x-ray detector.

6. The apparatus as claimed in claim 1, including an upper surface supported by side walls and covering the drive mechanism, the upper surface having respective annular slots formed therein which are coincident with the outer and inner rings, the first and second supports extending upwardly through the respective slots so that the x-ray generator and x-ray detector mounted on the first and second supports, respectively, are positioned above the upper surface.

7. The apparatus as claimed in claim 1, wherein the first and second supports are provided with a mechanism that raises and lowers the x-ray generator and x-ray detector mounted on the first and second supports, respectively, so as to enable objects to be scanned at different heights above an associated floor level.

8. The apparatus as claimed in claim 1, including a computer configured to enable the drive mechanism to be controlled by an associated operator.

9. The apparatus as claimed in claim 1, wherein the associated object to be scanned is an associated limb of an associated animal and the apparatus includes a head support that operatively engages the associated head of the associated animal.

10. The apparatus as claimed in claim 4, wherein the second rotary gear interengages with the teeth of the inner ring via the toothed drive belt, and the toothed drive belt extends around the toothed outer surface of the inner ring and around the toothed central hub.

11. The apparatus as claimed in claim 4, wherein the second rotary gear interengages with the teeth of the inner ring via the toothed, third rotary gear, the teeth of the third rotary gear interengaging with the teeth of the second rotary gear.

12. The apparatus as claimed in claim 10, wherein the gearing arrangement includes a tensioner positioned between the outer and inner rings to tension the toothed drive belt.

13. The apparatus as claimed in claim 5, wherein the cable handling mechanism for the cable supplying power to the x-ray generator comprises an elongate member housing the cable and secured at one end to the first support for the x-ray generator so as to move with the first support and secured at the other end to a non-moving element of the apparatus, and an annular channel within which the elongate member is constrained and which surrounds the outer ring.

14. The apparatus as claimed in claim 5, wherein the cable handling mechanism for the cable supplying power to the x-ray detector comprises an elongate member housing the cable and secured at one end to the first support for the x-ray detector so as to move with the first support and secured at the other end to a non-moving element of the apparatus, and an annular channel within which the elongate member is contained and which surrounds the inner ring.

15. The apparatus as claimed in claim 6, wherein brushes are attached to edges of each of the slots to inhibit associated dirt and solid materials falling through the slots and interfering with the outer and inner rings.

16. The apparatus as claimed in claim 8, wherein the computer is configured to receive, store and process data from the x-ray detector to produce one or more images.

17. The apparatus as claim in claim 8, including a shield for protecting the associated operator from x-ray radiation emitted by the x-ray generator.

18. The apparatus as claimed in claim 17, wherein the computer, the shield and the head support are provided in a single control station used by the associated operator.

* * * * *